US008449837B2

(12) United States Patent
Levchenko et al.

(10) Patent No.: US 8,449,837 B2
(45) Date of Patent: May 28, 2013

(54) MICROFLUIDIC DEVICE FOR HIGH-THROUGHPUT CELLULAR GRADIENT AND DOSE RESPONSE STUDIES

(75) Inventors: Andre Levchenko, Ellicott City, MD (US); Alexander Groisman, San Diego, CA (US); Saurabh Paliwal, Baltimore, MD (US)

(73) Assignees: The Johns Hopkins University, Baltimore, MD (US); UCSD Tech Transfer Office, La Jolla, CA (US)

( * ) Notice: Subject to any disclaimer, the term of this patent is extended or adjusted under 35 U.S.C. 154(b) by 863 days.

(21) Appl. No.: 12/083,480

(22) PCT Filed: Oct. 11, 2006

(86) PCT No.: PCT/US2006/040030
§ 371 (c)(1),
(2), (4) Date: Oct. 13, 2009

(87) PCT Pub. No.: WO2007/044888
PCT Pub. Date: Apr. 19, 2007

(65) Prior Publication Data
US 2010/0035292 A1 Feb. 11, 2010

Related U.S. Application Data

(60) Provisional application No. 60/725,416, filed on Oct. 11, 2005.

(51) Int. Cl.
*G01N 13/00* (2006.01)
*C12Q 1/02* (2006.01)
(52) U.S. Cl.
USPC .......................................... 422/502; 73/64.47

(58) Field of Classification Search
None
See application file for complete search history.

(56) References Cited

U.S. PATENT DOCUMENTS

| 5,376,252 A | 12/1994 | Ekstrom et al. |
| 5,876,946 A | 3/1999 | Burbaum et al. |
| 5,942,443 A | 8/1999 | Parce et al. |
| 5,989,835 A | 11/1999 | Dunlay et al. |
| 6,071,478 A | 6/2000 | Chow |
| 6,086,740 A | 7/2000 | Kennedy |

(Continued)

FOREIGN PATENT DOCUMENTS
WO WO-2007044888 A3 * 4/2007

OTHER PUBLICATIONS

Yun et al., "Micro/Nanofluidic Device for Single-Cell-Based Assay", *Biomedical Microdevices* 7:1, 35-40 (2005).

(Continued)

*Primary Examiner* — In Suk Bullock
*Assistant Examiner* — Paul Hyun
(74) *Attorney, Agent, or Firm* — Edwards Wildman Palmer LLP; Peter F. Corless, Esq.; Richard B. Emmons

(57) ABSTRACT

The ability to form and maintain gradients is essential for the study of response of cells to various stimuli. The invention includes devices and methods for the high-throughput, reproducible formation of gradients for the study of living cells. The invention includes microfluidics device with a test chamber having a depth flanked by flow-through channels having a deeper depth. Flow of two different fluids through the flow-through channels results in the creation of a gradient by diffusion across the test chamber having essentially no flow.

23 Claims, 4 Drawing Sheets

U.S. PATENT DOCUMENTS

| | | |
|---|---|---|
| 6,238,538 B1 | 5/2001 | Parce et al. |
| 6,274,337 B1 | 8/2001 | Parce et al. |
| 6,306,659 B1 | 10/2001 | Parce et al. |
| 6,368,871 B1 | 4/2002 | Christel et al. |
| 6,395,232 B1 * | 5/2002 | McBride .................. 422/504 |
| 6,399,952 B1 | 6/2002 | Maher et al. |
| 6,408,878 B2 | 6/2002 | Unger et al. |
| 6,429,025 B1 | 8/2002 | Parce et al. |
| 6,479,299 B1 | 11/2002 | Parce et al. |
| 6,488,895 B1 | 12/2002 | Kennedy |
| 6,551,841 B1 | 4/2003 | Wilding et al. |
| 6,573,039 B1 | 6/2003 | Dunlay et al. |
| 6,585,939 B1 | 7/2003 | Dapprich |
| 6,614,030 B2 | 9/2003 | Maher et al. |
| 6,620,591 B1 | 9/2003 | Dunlay et al. |
| 6,632,656 B1 | 10/2003 | Thomas et al. |
| 6,653,124 B1 | 11/2003 | Freeman |
| 6,716,588 B2 | 4/2004 | Sammak et al. |
| 6,727,071 B1 | 4/2004 | Dunlay et al. |
| 6,759,206 B1 | 7/2004 | Rubin et al. |
| 6,818,435 B2 | 11/2004 | Carvalho et al. |
| 6,838,680 B2 | 1/2005 | Maher et al. |
| 6,857,449 B1 | 2/2005 | Chow |
| 6,875,578 B2 | 4/2005 | Giuliano et al. |
| 6,951,632 B2 | 10/2005 | Unger et al. |
| 7,005,292 B2 | 2/2006 | Wilding et al. |
| 7,018,830 B2 | 3/2006 | Wilding et al. |
| 7,040,338 B2 | 5/2006 | Unger et al. |
| 7,060,445 B1 | 6/2006 | Dunlay et al. |
| 7,067,263 B2 | 6/2006 | Parce et al. |
| 7,117,098 B1 | 10/2006 | Dunlay et al. |
| 7,143,785 B2 | 12/2006 | Maerkl et al. |
| 7,160,687 B1 | 1/2007 | Kapur et al. |
| 7,216,671 B2 | 5/2007 | Unger et al. |
| 7,223,363 B2 | 5/2007 | McNeely et al. |
| 7,235,373 B2 | 6/2007 | Dunlay et al. |
| 7,376,256 B2 | 5/2008 | Kirsch et al. |
| 7,378,280 B2 | 5/2008 | Quake et al. |
| 7,452,726 B2 | 11/2008 | Chou et al. |
| 7,476,363 B2 | 1/2009 | Unger et al. |
| 7,494,555 B2 | 2/2009 | Unger et al. |
| 7,601,270 B1 | 10/2009 | Unger et al. |
| 7,939,018 B2 | 5/2011 | Bedingham et al. |
| 2002/0005354 A1 * | 1/2002 | Spence et al. ............. 204/450 |
| 2002/0168757 A1 * | 11/2002 | Kirk et al. ............. 435/288.5 |
| 2003/0096310 A1 | 5/2003 | Hansen et al. |
| 2004/0115838 A1 | 6/2004 | Quake et al. |
| 2005/0266582 A1 * | 12/2005 | Modlin et al. ............ 436/164 |
| 2006/0194273 A1 | 8/2006 | Thomas |
| 2007/0196912 A1 | 8/2007 | Facer et al. |
| 2007/0253868 A1 * | 11/2007 | Beebe et al. ............. 422/100 |
| 2009/0239292 A1 | 9/2009 | Thomas et al. |
| 2010/0028928 A1 | 2/2010 | Levchenko et al. |
| 2011/0003372 A1 * | 1/2011 | Jeon et al. ............. 435/287.3 |

OTHER PUBLICATIONS

Gu et al., "Computerized Microfluidic Cell Culture Using Elastomeric Channels and Braille Displays", *PNAS*, vol. 100, No. 45, 15861-15866 (2004).

Thorsen et al., "Microfluidic Large-Scale Integration", *Science Magazine*, vol. 298, p. 580-584 (2002).

Unger et al., "Monolithic Microfabricated Valves and Pumps by Multilayer Soft Lithography", *Science Magazine*, vol. 288, p. 113-116 (2000).

International Search Report, International Application No. PCT/US2006/40030, dated Mar. 26, 2008.

* cited by examiner

MICROFLUIDIC DEVICE FOR HIGH-THROUGHPUT CELLULAR GRADIENT AND DOSE RESPONSE STUDIES

RELATED APPLICATIONS

This application claims the benefit of U.S. Provisional Application No. 60/725,416 filed Oct. 11, 2005. The entire contents of the aforementioned application are hereby incorporated herein by reference.

BACKGROUND OF THE INVENTION

The ability to form and maintain gradients is essential for the study of response of cells to various stimuli. In nature, concentration gradients of different chemicals cause chemoattraction and repulsion in processes including neuronal growth, immune response, and signaling in single cell organisms. Methods for establishing gradients for tissue culture have mostly involved patterning of cell adhesion molecules on glass slides or cover glasses (Dertinger et al., 2002. *PNAS* 99: 12542-12547). Such methods result in the formation of stable and reproducible gradients; however, they are useful only for adherent cells. Adherent cells can also be exposed to gradients by flowing over the cells a stream with an imbedded gradient of an active agent. However, this method also results in the exposure of the cells to shear stress, potentially creating artifacts and skewing results. In addition, this method is not applicable to non-adherent cells, unless they are made adherent through non-physiological means.

Methods for establishing gradients of chemoattractants and other agents for the study of adherent or non-adherent cells are frequently relatively primitive. For example, Janetopoulus et al. (2004. *PNAS* 101: 8951-8956) established gradients to study the response of *Dictyostelium discodeum* cells to chemoattractants by application of the chemoattractant using a micropipette in an open system. The method allows for rapid modification of spatial and temporal stimuli; however, it has a low throughput and the shape of the established gradient is difficult to measure and to reproduce.

There is a need for a device and method for reproducible, high throughput analysis of response of cells, both adherent and non-adherent, to gradients of active agents.

SUMMARY OF THE INVENTION

The invention includes microfluidics devices for the establishment and maintenance of gradient profiles with essentially no flow in the region, where a gradient profile is established, in particular, there is preferably no flow over cells exposed to the gradient. The invention also includes methods of use of the microfluidics devices of the invention. The gradients are created by diffusion of chemicals (active agents) across a test chamber, between reservoirs (flow-through channels) with different concentrations of the chemicals. The concentrations of the chemicals in the reservoirs are maintained constant over time by continuous perfusion with stock solutions of desired concentrations. The devices are designed in such a way that, in spite of the perfusion flow through the reservoirs, there is no flow in the regions between the reservoirs where the gradient profiles are established.

Devices of the invention include at least one reaction unit, wherein the reaction unit includes a series of fluid channels of at least two different depths. The fluid channels include a series of test chambers having a first depth, which are flanked by first and second flow-through channels preferably having a deeper depth than the test chambers, and connection channels can be of any depth within the tolerance of fabrication and function of the devices. The connection channels operably connect the fluid channels to inlet ports and outlet ports for the introduction and removal of cells, buffers, and active agents. Flow through the fluid channels preferably is controlled by a series of pressure-actuated valves that are operably linked to controllers via control channels.

The flow-through channels of the device preferably include at least the following characteristics. First, the flow-through channels can be connected a short distance downstream from the test chambers where the flow-through channels merge, and the pressures in the flow-through channels preferably are equilibrated at the connection point. Second, the flow-through channels can be mirror-symmetric with respect to each other and the flow rates in them adjusted to be equal, leading to equal pressures at the opposite sides of the test chambers, which are connected to the two flow-through channels. This equal pressure across the test chambers results in the creation of a gradient across the test chambers with essentially no flow, due to the relatively higher resistance to flow in the test chambers as compared to the flow-through channels.

The microfluidic devices of the invention contain at least two layers that are separately formed and subsequently fused together to form the final device. The fluid channels are present in the flow layer, typically the bottom layer, of the microfluidic device. The test chambers and flow-through channels preferably have rectangular, cross-sectional profiles for generating well-defined, easy to model flow environments. The connection channels have rounded cross-sectional profiles to allow the tight sealing of these channels with pressure-actuated valves activated through channels in the control layer. The channels in the flow layer and in the control layer are separated by flexible membranes in areas where they overlap. The membranes can be about 100 microns thick and serve as pressure-actuated valves for closing and opening the flow layer channels. The devices of the invention are typically bound to glass slides or coverslips.

The invention includes the use of the device of the invention to create gradients, preferably for the study of cells in response to gradients. Prior to the formation of the gradient, flow-through channel valves are closed to allow for the seeding of cells into the test chambers, optionally after coating the test chambers with a compound to modulate cell adhesion. The flow-through channels must be closed for cells to enter the test chambers as the resistance to flow is substantially higher in the test chambers than the flow-through channels. Cells are introduced into the test chambers through the cell inlet port via the connection channel. Next, a first fluid and a second fluid are introduced first flow-through channel of the device and the second flow-through channel of the device, respectively. Pressure in the flow-through channels is equalized where the connection channels merge. Fluid is passed through the flow-through channels in the direction indicated in the figures to create a gradient formed by diffusion of the molecules present in the first fluid and the second fluid across the test chambers. Typically, the first fluid is a buffer solution or a medium with an active agent (e.g., agonist, stimulant, ligand, chemoattractant), and the second fluid is the buffer solution or the medium with no active agent. In another embodiment, both the first and second fluid may contain an active agent. The active agents may be different concentrations of the same active agent, or two different active agents. In yet another embodiment, the first fluid and second fluid may each, independently contain more than one active agent. The direction of the gradient can be rapidly reversed by switching the flow-through channels into which the first fluid and second fluid are introduced. Cells can be visualized continuously (e.g., by video microscopy) or at intervals while being continuously subjected to the gradient. The device can be attached to a warmer to maintain the temperature of the fluid within the device, either by maintaining the temperature of the fluid being fed to the flow-through channels or by heating the device itself. Alternatively, the device can be used with a stage warmer. The device can also be used in conjunction with a $CO_2$ chamber for gas, humidity and temperature control with mammalian cells.

DEFINITIONS

Figure 1A:
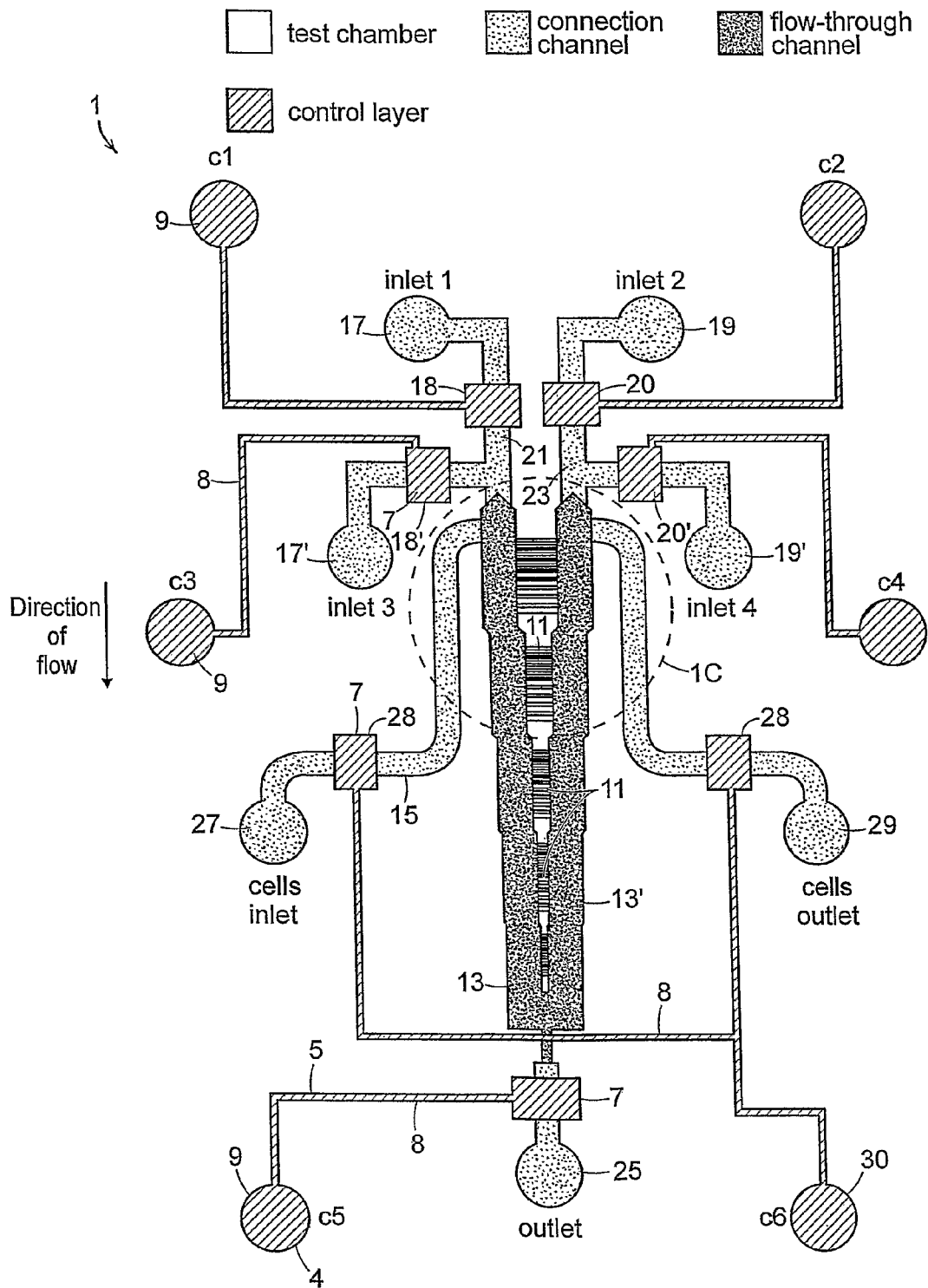
FIG. 1A is a schematic plan view of a microfluidics device according to a preferred embodiment of the invention depicting test chambers arranged in a progressively narrowing space between flow-through channels.

The instant invention is most clearly understood with reference to the following definitions.

A "fluid layer" is any layer of a device in which fluid channels are incorporated. In the context of the instant invention, the fluid layer is typically the bottom layer of the device.

A "fluid channel" is a channel through which fluid and/or air can flow wherein the channel is part of the fluid layer. Fluid channels are functionally connected to both inlet and outlet ports optionally by connection through other fluid channels. Fluid channels are preferably rounded to improve sealing of the fluid channels by valves.

A "flow-through channel" is a low resistance flow channel, about 25 microns to about 150 microns deep, preferably about 50 microns to about 100 microns deep. Flow-through channels are sufficiently wide (perpendicular to the direction of flow) to not inhibit the flow of fluid through the channel, and not excessively wide to inhibit the function of valves. Such considerations are well understood by those of ordinary skill in the art. In devices of the instant invention, paired flow-through channels flank test chambers with higher resistance to flow. Flow-through channels are connected to each other a short distance downstream from the test chambers where the flow-through channels merge, and the pressures in the flow-through channels are equilibrated at the connection point. Additionally, flow-through channels are mirror-symmetric with respect to each other and the flow rates in them are adjusted to be equal, leading to equal pressures at the opposite sides of the test chambers, which are connected to the two flow-through channels.

"Test chambers" are a series of chambers interposed between two flow-through channels for seeding of cells and formation of gradients. The test chambers are also defined by elevated ridges that extend laterally between the flow-through channels. Resistance of fluid flow through the test chambers is higher than the resistance in the flow-through channels, resulting in the creation of a gradient across the test chambers essentially without flow. This resistance is typically established by having test chambers that are substantially and sufficiently shallower than the adjacent flow-through channels to create resistance such that there is essentially no flow in the test chambers. Such parameters can be readily determined by one of ordinary skill in the art using mathematical or empirical modeling. The size of a test chambers is also dependent on the type of cells to be exposed to the gradient with larger (e.g., mammalian cells) requiring larger test chambers.

A "reaction unit" is a unit by which the microfluidic devices of the invention are organized. A reaction unit includes at least one inlet port and a single outlet port operably connected to each a pair of flow-through channels wherein the ports are connected to the flow-through channels by connection channels. Flow-through channels are connected by test chambers located between the flow-through channels. The test chambers are operably connected to at least one cell inlet port and one cell outlet port for the loading of cells into the test chambers. The flow-through channels in the figures are indicated by heavy stippling.

A "control layer" is the layer in which controllers, control channels, and valves are incorporated. In a preferred embodiment of the invention, the control layer is the top layer of the device. The control layer in the figures is indicated by hatch marks.

A "valve" is a component of the device that regulates flow through a fluid channel of the device by substantially inhibiting flow through the fluid channel upon closure. Substantially inhibiting the flow means that flow is inhibited at least 80%, preferably at least 90%, more preferably at least 95%, even more preferably at least 99%, most preferably flow is completely (i.e., 100%) inhibited. In a preferred embodiment, a valve is a portion of a dead end channel (i.e., open on one end only at a control layer inlet). The valve is located adjacent to, typically above, a channel in the fluid layer and is sufficiently wide to inhibit and preferably close off flow through the adjacent fluid channel. The size of the valve is dependent on the size and shape of the fluid channel and the amount of pressure required to close the valve. In a preferred method, the fluid channel is about 250 microns wide and the valve is about 300 microns wide. The channel and control valve cross perpendicularly. Upon actuation of the valve, preferably by hydrostatic pressure, the channel closes and opens.

A "valve controller" is the opening in the control layer at the end of a control channel, distal from the valve(s), that can be operably linked to a device (e.g., a syringe) to modulate the pressure in the control channel.

A "control channel" operably links a valve controller to its valve(s). A control channel is sufficiently narrow (about 80 microns wide when the channels are about 250 microns wide) so that closure of the linked valve(s) through the valve controller does not substantially interfere with fluid flow in the fluid channels adjacent to the control channel. The critical ratio of the width of the control channel to the fluid channel may also depend on the height of the fluid channel and the thickness of the bottom layer; however, the ratio of the control to fluid channel is preferably about less than 0.25 to not substantially interfere with flow. Substantially interfere is understood as not decreasing fluid flow by more than 50%, preferably not decreasing fluid flow by more than 40%, more preferably not decreasing fluid flow by more than 30%, even more preferably not decreasing fluid flow by more than 20%, most preferably not decreasing fluid flow by more than 10%.

An "elastomeric compound" or "elastomer" is a rubber. Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

A "compound to modulate cell adhesion" includes natural compounds, such as an extracellular matrix (ECM) component is a protein (e.g., fibronectin, laminin, integrin, collagen), peptide (e.g., RGD binding site), carbohydrate, or other chemical compound (e.g., extracellular signaling molecule) present in the ECM that controls cell attachment and/or migration. Non-ECM components (e.g., poly-lysine, gelatin, antibodies) are also known to modulate cell adhesion. Compounds to modulate cell adhesion in the instant invention preferably promote cell adhesion.

An "active agent" is a compound that modulates the activity of a cell or can be visualized using microscopy. Active agents include, but are not limited to, a naturally or non-naturally occurring molecules including agonists, antagonists, chemoattractants, chemorepellants, nutrient sources, mating factors, signal transduction molecules, peptides, carbohydrates, nucleic acids, drugs or therapeutic agents, dyes, and fluorescent tags.

"Essentially no flow" is understood as the rate of flow in the test chambers is less than about 10% than that in the direction of fluid flow in the flow-through channels, as indicated in the figures. In a preferred embodiment, the rate of flow in the test chamber is less than about 5%, more preferably less than about 1%, most preferably less than about 0.1% of the flow rate in the flow-through channels in the device as indicated in the figures.

DETAILED DESCRIPTION OF THE INVENTION

The instant invention is directed to microfluidics devices for the formation of gradients, preferably of active agents, to study the effects of gradients of active agents on living cells. The device creates gradients across test chambers with essentially no flow, allowing for the study of both adherent and non-adherent cells. The device is composed of a chip made of an optically clear, biocompatible polymer, such as PDMS, with microchannels engraved in it, which is sealed to a glass support, such as a cover slip. The mounting can be reversible to allow for the device to be cleaned and re-used. The device can also be mounted to a heater to maintain the temperature of the device throughout the experiment. During live cell imaging, a stage warmer can be used. A $CO_2$ chamber can also be used with mammalian cells. Such devices are well known to those skilled in the art. Cells can be imaged using any of a number of optics and contrast methods including, but not limited to light, fluorescence, and phase contrast microscopy. Images may be captured using analog or digital methods using manual or automated devices. Methods and devices for microscopy and image capture are well known to those skilled in the art.

The device is composed of a plurality of layers, preferably two layers, a fluid layer and a control layer. The fluid layer is adjacent to the glass support. Typically, when cells are seeded into the device, they attach to the glass support on which the device is mounted. The fluid channels are rounded for optimal function of the valves. All fluid channels are operably connected to both an inlet and an outlet port, optionally by other fluid channels. Fluid flow through channels is controlled by valves present in the control layer. The valves are operably linked to controllers via channels in the control layer. Control channels are typically dead-end channels. They terminate within the control layer, typically at a valve, and are connected to a single port serving as both an inlet and outlet (i.e., the controller). One or more valves can be controlled by a single controller by operably linking the valves to a single control port, or a valve can be of a dimension such that control of fluid flow through more than one fluid channel is modulated by actuation of a single controller. The use of a series of valves that control fluid flow through more than one fluid channel in the device of the invention allows for the device of the invention to be high throughput.

A reaction unit includes a series of test chambers that are flanked by two flow-through channels. The gradient is created by a combination of the first fluid in the first flow-through channel, and the second fluid in the second flow-through channel, wherein at least either the first fluid or the second fluid contains an active agent, either a different concentration of the same active agent in each fluid, or different active agents in each fluid. However, it is possible for both the first fluid and the second fluid to include an active agent. The flow-through channels can be operably connected to more than one inlet port wherein each inlet port is preferably controlled by an independent controller. This arrangement allow for rapid switching of the composition of the fluid in each flow-through channel, allowing for the direction or the composition of the gradient to be changed rapidly without flushing the reaction unit.

Multiple reaction units can be included in a single device. The inlet ports can be fabricated such that the first fluid for each of a plurality of first flow-through channels is delivered through a first inlet port, and the second fluid for each of a plurality of second flow-through channels is delivered through a second inlet port. This provides for maximum reproducibility between multiple gradients for testing the response of multiple cell types (e.g., wild type cells and cells containing mutations; neutrophils, eosinophils, mast cells, other immune cells) to a single gradient. The size, depth and length, of the test chamber can be varied dependent on the size of the cell type to be analyzed.

In the actual microfabricated devices, there is always some disparity between the flow-through channels, and the adjustment of the flow rates in them is always somewhat imperfect. These both factors, lead to differences in pressure between the opposite sides of test chambers that are typically on the order of 1% of the pressure required to drive the flow in the flow-through channel. These unintended pressure differences lead to flow through the chambers that, when sufficiently strong, can have a detrimental effect on the gradient profiles and on cells in the chambers. As the materials and methods become available to fabricate the devices of the instant invention with greater precision, the less difference will be required in the depth of the flow-through channels and the test chambers. Theoretically, a device with sufficient precision could have flow channels the same depth as test chambers. To reduce the flow through the test chambers, they are made much shallower than the flow-through channels. For example, in one of the embodiments of the device, the test chambers are microns deep, whereas the flow-through channels have a 20 time larger depth of 100 microns. At a given pressure difference, the volumetric flow rate through a channel is proportional to the channel depth cubed. Therefore, the volumetric flow rate in a test chamber is expected to be 8000 times lower that in a flow-through channel at the same pressure difference and ~$10^6$ times lower, if the pressure difference across the chamber is ~1% of the pressure difference in the flow-through channel. In practice, the flow rate through the test chambers is practically undetectable and has no effect on either cells or gradient profiles.

Devices and methods of the instant invention can be used for the analysis of the effects of gradients on a number of cell types in response to various agents.

Devices and methods of the invention can be used to screen the dose response of cells to various drugs, growth factors, antibodies, cytokines and similar bio-active agents, even if these agents are not chemotactic. A range of concentrations of drug required to induce specific changes in cell morphology, protein expression, growth rates can be analyzed using the devices and methods of the invention. As many drugs are given in combination with other drugs, the device can be used to analyze synergistic and additive effects of drugs in complex gradients wherein the first drug (i.e., active agent) is passed through the first flow-through channel, and a second drug is passed through the second flow-through channel. Such methods for dose response analysis of drugs and other pharmacological agents are well within the ability of those skilled in the art.

Further examples include, but are not limited to the study of the effects of chemoattractant gradients on amoebae *Disctyostelium discoideum*; the effects of VEGF and other growth factors on locomotion of Human Vascular Endothelial cells and other types of endothelial cells; the analysis of motile cells capble of directed migration (chemotaxis) in response to gradients of extracellular chemical cues (chemoattractants and chemorepellents); the analysis of migrationon of growth cones of human nuetrophils; analysis of human and *Xenopus laevis* neuronal growth cone and axon guidance in the presence chemoattractant or chemorepellant guidance cues; Bacterial chemotaxis studies, including chemtoaxis studies of extracellular (e.g. *Escherichia coli*) or intracellular (e.g. *Listeria monocytogenes*) pathogens in the human body; chemotaxis studies of metastatic tumor cells; analysis of migration of neuronal and cardiac stem cells; study of fibroblast chemotaxis during wound healing; studies of T-cell chemotaxis and modeling T-cell migration during immune response; and analysis of chemotactic drug targeting by combining drug molecules with selective ligands, potentially involving chemorepellant ligands to prevent drug breakdown by non-target cells as well as chemotactic ligands to accumulate and target specific cell types. As within the gradient cells are exposed to different concentrations of the agent in different parts of the test chambers, the dose response can be readily achieved. The results of dose response experiments can be quantified using either fluorescent probes within cells (live cell imaging), or by any other staining means, e.g. immunocytochemistry following experiment cessation. The list is by no means a limitation of the invention. Other uses of the devices and methods of the invention are well within the ability of those skilled in the art.

Test chambers can be seeded with a single cell type or multiple cell types. In the embodiments shown in FIGS. 1A and 1B, the width of the test chambers progressively narrows (in an exponential fashion) perpendicular to the direction of fluid flow. This results in a gradient wherein the change in the concentration of the active agent is exponential in a direction perpendicular to the flow in the flow-through channels (i.e. shorter distance between the flow-through channels resulting in a steeper gradient). In such an embodiment, a single cell type is seeded in a series test chambers between two flow-through channels. This results in a number of linear concentration profiles with varying gradient slopes, where the gradients with the maximum slope are created in the test chambers that are the narrowest. This allows for the response of the cells to the gradient to be tested over a large range of gradients (1-2 orders of magnitude difference).

In an alternative embodiment of the device of the invention (not shown) the series of test chambers is rectangular in shape, meaning of a constant width in the direction of flow in the flow-through channels. In such an embodiment, the change in the concentration over the width of the test chamber, perpendicular to the direction of fluid flow in the flow-through channels, is linear rather than logarithmic. Gradients in rectangular and trapezoidal shaped test chambers can be described by the equations below.

Test chambers with rectangular shapes in the plane of the device have a constant cross-sectional area, resulting in a linear variation of concentration between the flow-through channels (the source and sink). For a substance with a diffusivity D the diffusive flux in the x-direction per unit area is given by $j=-D\partial c(x)/\partial x$, where $c(x)$ is the local concentration of the substance. For a channel with a depth h and a width w the total flux at the position x is given by $J=-Dhw\partial c(x)/\partial x$. In a state of equilibrium, by conservation of mass we have $J=const$, so $w\partial c(x)/\partial x=const$ for a test chamber of a constant depth, h. If the chamber width remains constant as well, we have $\partial c(x)/\partial x=const$, with a linear profile solution $c(x)=c_0+(c_1-c_0)x/L$ that becomes $c(x)=(c_1/L)x$, when the concentration in the left flow-through channels is zero. However, if the chambers width varies, the concentration profile is non-linear. For example, for a linear variation of the chamber width (chamber in the middle in FIG. 3), $w(x)=w_0+(w_1-w_0)x/L$, the profile is logarithmic (where $w_0$ and $w_1$ are chamber widths at the left and right sides, respectively). For an exponential variation of chamber width, $w(x)=w_0 \exp(-ax)$, the profile is exponential, with a shape $c(x)=A \exp(ax)+B$, where the constants A and B are defined by the concentrations in the flow-through channels, $c_0$ and $c_1$. Importantly, when the concentrations are chosen so that $c_0/c_1=w_1/w_0$, the concentration profile is expected to have a particularly simple exponential shape $c(x)=c_0 \exp(ax)$. Exponential concentration profiles have a special feature of constant fractional gradients, $$\frac{1}{c}\frac{\partial c}{\partial x},$$

and thus constant fractional (percentage) differences of concentration over any given distance, e.g. the diameter of a cell. Therefore, exponential concentration profiles are particularly appealing for experiments on gradient sensing of cells of different types (yeast, neutrophils, *D. Discodeum*, etc).

Figure 2:
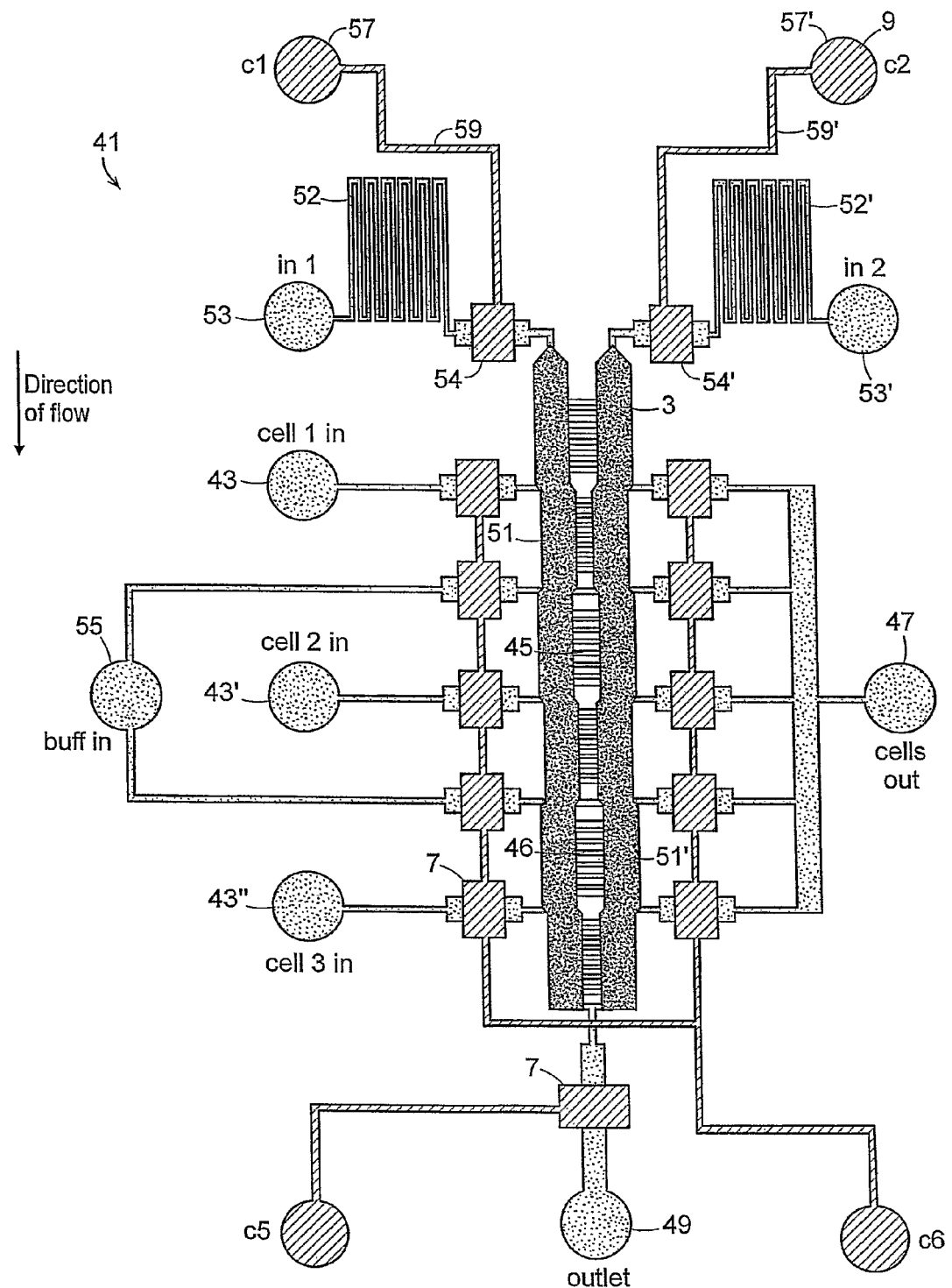
FIG. 2 is a schematic plan view of a microfluidics device according to a third preferred embodiment of the invention depicting test chambers with sides that are essentially parallel to the direction of fluid flow through the device, and having at least two different widths in a plane of the flow-through channels.

In FIG. 2, a third preferred embodiment of the invention is shown wherein multiple cell lines or strains are exposed to gradients created by the media flowing through common flow-through channels. Multiple cell types can be introduced simultaneously into their respective test chambers through channels (connected to cell inlet ports) perpendicular to the flow-through channels. The flow streams containing multiple cell types or strains are separated from each other by flow streams of plain buffer (or plain media) introduced at the same time as the introduction of the cell lines or strains. This ensures that there is no mixing of different cell lines or strains in their respective test chambers, thus avoiding contamination of the experimental results. The inlet channels for introducing the buffer, which are fed by an inlet port for the buffer, are also perpendicular to the flow-through channels and lie between the inlet channels for the cell strains. The alternating widths of the test chamber, perpendicular to the direction of fluid flow of the flow-through channels, produces repetitive gradients (along the length of the test chamber). As the device of the invention creates gradient with essentially no flow, the cells are not flushed out of the test chamber. This embodiment allows for the testing of multiple cell types in a single reaction unit.

Gradients can be observed by fluorescence imaging using a fluorescent dye, preferably a dye with approximately the same diffusivity as the active factor to be tested in the gradient. The optimal concentration of the dye depends on a number of factors including, but not limited to the intensity of its fluorescence and its tendency to decay under fluorescence illumination, and potential toxicity or other side effects to the cells. Such considerations are well known to those skilled in the art.

Fluids can be introduced into the devices of the invention using modified syringes to which external air pressure can be applied. The syringes are connected to Tygon tubing (Cole Palmer, ID 0.02"), and capped by a metallic tip tightly inserted into the chip inlet. Syringes are then mounted on sliding platforms and fixed at different heights to control hydrostatic pressure at inlets and outlets. Pressure regulation of syringes can also be performed using syringe pumps. Plain water can be used for the valve control inlets.

Representative examples of the devices of the instant invention are shown in the figures. It is understood that a plurality of an element may exist in the device when only one of the elements is noted herein or in the drawing.

FIG. 1A depicts a single cell type reaction unit 1. As shown, the series of test chambers progressively narrows between the flow-though channels (i.e., the space between the flow-through channels in a plane of flow in the device is essentially a trapezoid in a plane of the flow-through channels of the device). The direction of fluid flow is indicated next to the device. Multiple reaction units can be cast into a single microfluidics device. The reaction unit includes a fluid layer (indicated by no texture and stippled textures) and a control layer (indicated by cross-hatching). The control layer includes a number of valves 7 that are operably linked through valve control channels 8 to valve controllers 9 that can be actuated by air or fluid (e.g., using a syringe, not shown) to regulate the valves. Upon actuation of the valve, flow through the fluid channel is substantially inhibited.

The fluid layer includes a series of test chambers 11 that are flanked by two flow-through channels 13 and 13' (indicated by a heavily stippled texture). The two channels merge at the bottom of the flow-through channels to equalize the pressure in the channels. Test chambers 11 are defined by two flow-through channels, 13 and 13', on either side, and elevated ridges 10 above and below the test chambers that extend laterally between the flow-through channels, relative to the direction of fluid flow through the fluid channels. Resistance of fluid flow through the test chambers is higher than the resistance in the flow-through channels, resulting in the creation of a gradient across the test chambers essentially without flow. This resistance is typically established by having test chambers that are substantially and sufficiently shallower than the adjacent flow-through channels to create resistance such that there is essentially no flow in the test chambers. Such parameters can be readily determined by one of ordinary skill in the art using mathematical or empirical modeling. The size of a test chambers is also dependent on the type of cells to be exposed to the gradient with larger (e.g., mammalian cells) requiring larger test chambers.

FIG. 1A depicts the series of test chambers having cross-sectional areas that decreases corresponding to the direction of flow through the reaction unit. In an alternative embodiment, the spacing between the flow-through channels is substantially constant along the length of the series of test chambers (i.e., the space between the flow-through channels in a plane of flow in the device is essentially a rectangle in a plane of the flow-through channels of the device). The test chambers preferably are less than about one half, more preferably less than about one fifth, most preferably less than about one tenth the depth of the flow-through channels. In a preferred embodiment of the invention, the flow-through channels are between about 25 microns and about 150 microns deep. In a more preferred embodiment of the invention, the flow-through channels are between about 30 microns and about 120 microns deep. In a most preferred embodiment, the flow-through channels are about 40 microns to about 100 microns deep. The depth of the flow-through channels is essentially the same throughout the channel, within the tolerances of the fabrication method.

In a preferred embodiment of the invention, the test chambers are about 1 micron to about 20 microns deep. The depth of the test chambers is dependent upon a number of factors including, but not limited to, the size of the cells to be exposed to the gradient and the depth of the flow-through channels. In a preferred embodiment, test chambers for eukaryotic cells are about 1 micron to about 5 micron in depth; test chambers for yeast are about 3 microns to about 7 microns in depth; and test chambers for mammalian cells are about 10 to about 20 microns in depth. Methods of calculating gradients are provided in the examples. It is within the ability of those skilled in the art to determine optimal depths and ratios of depths of test chambers to flow-through channels depending on the desired shape, steepness, and range of the gradient desired.

Connection channels may be essentially any depth within the tolerances of the fabrication and use of the devices of the invention. For example, connection channels must be sufficiently large to delivery sufficient fluids to flow-through channels without inhibiting flow. However, connection channels must be small enough to be fabricated and effectively closed by valves. Such considerations are well understood to those skilled in the art.

Cells are introduced into the test chambers through a cell inlet port 27 that is operably linked to the test chamber by cell fluid channel 15. Cells must be introduced into the test chambers with the flow-through channels closed as the resistance to flow is substantially higher in the test chambers than in the flow-through channels. Flow of cells through the device is controlled by cell fluid channel valves 28 which are, in turn, controlled by a cell channel valve controller 30 which is operably connected to the valves by a cell valve controller channel. In an alternative embodiment, each of the cell inlet port 27 and a cell outlet port 29 are controlled by independent valves and controllers.

Fluids are introduced into the flow-through channels 13 and 13' through the inlet ports 17 and 17', and 19 and 19' respectively, which are functionally connected to each other via fluid channels. Movement of fluid from the inlet ports to the flow-through channels is regulated by four independent valves, 18 and 18', and 20 and 20'. This allows for the rapid switching of compositions and/or directions of gradients by controlling flow through each of the inlets independently. Fluids flow through the reaction unit and exit via an outlet port 25. Flow through the outlet port is regulated by an outlet port valve 26 that is controlled via its corresponding outlet controller that is operably linked via the outlet controller channel the outlet port valve.

Figure 1B:
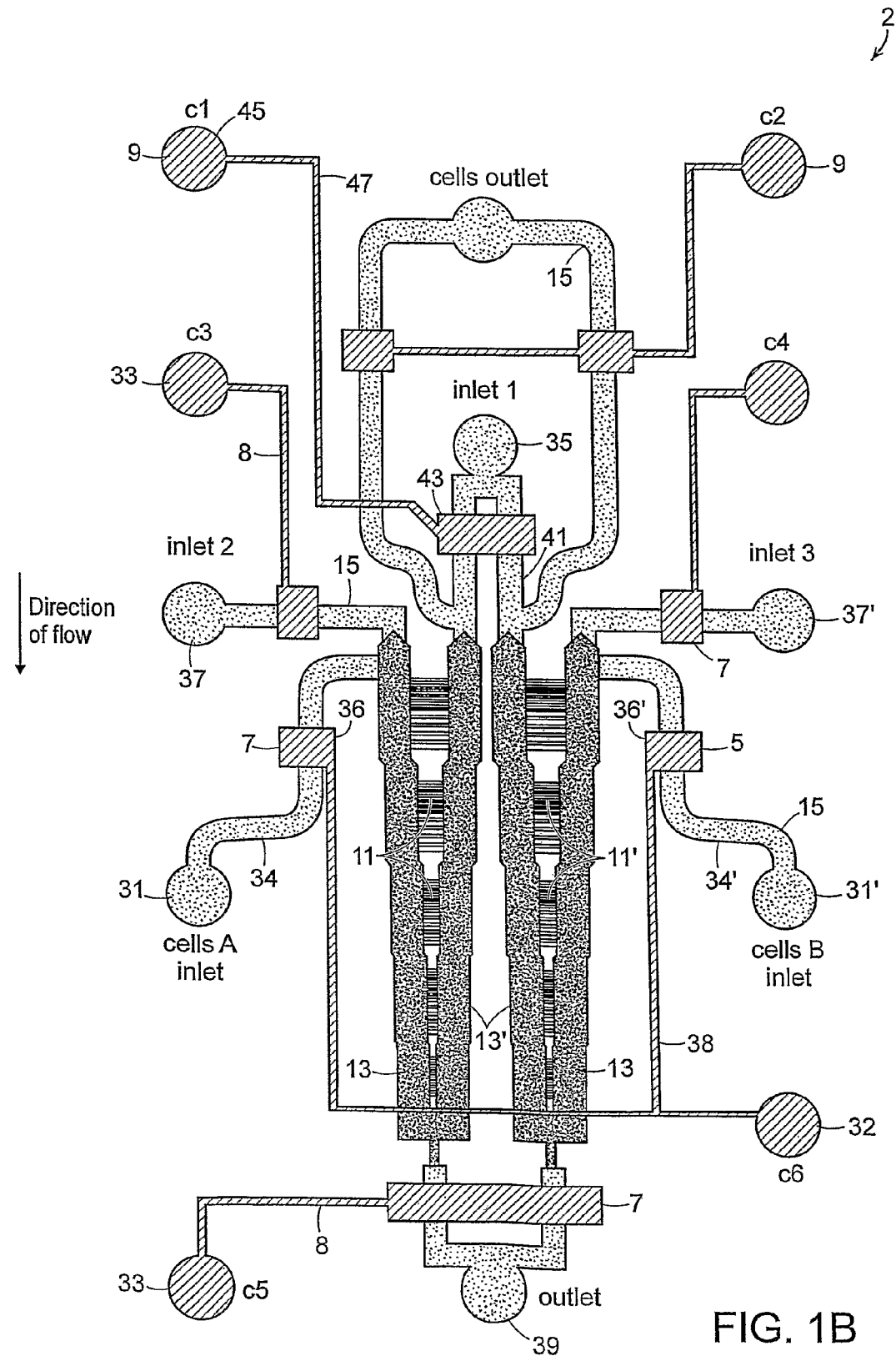
FIG. 1B is a schematic plan view of a microfluidics device according to a second preferred embodiment of the invention depicting two independent series of test chambers.

FIG. 1B depicts a second preferred embodiment of the invention that includes two sets of test chambers 11 and 11' for performing assays in parallel, preferably on two different cell types, wherein each series of test chambers contains a different cell type (e.g., wild type and mutant versions of yeast cells). Although such assays can be performed in multiple, independent reaction units, the paired reaction chamber has advantages including, but not limited to, ease of imaging of the two series of test chambers as they are closer together, and improved reproducibility of the gradient.

Cells are introduced through two different cell inlet ports, 31 and 31' which are operably linked to the test chambers via cell inlet channels, 34 and 34'. Flow through the cell inlet channels is controlled by a cell inlet control channel valves 36 and 36' which are operably linked to a cell inlet valve controller 32 via cell inlet valve control channel 38.

In the apparatus, fluid is introduced into the central flow-through channels 13' through a single inlet port 35 which is operably linked to the central flow-through channels 13' via a fluid connection channel 41. Flow-through fluid connection channel 41 is controlled by valve 43 via valve controller 45 which is operably linked via inlet control channel 47. Inlets 37 and 37' provide fluid access to the outside flow-through channels 13. If two cell types are being tested for their response to identical gradients, identical fluids are introduced through inlets the 37 and 37'. However, it is possible to test responses to two independent gradients using the apparatus by introducing two different fluids, preferably each containing a different active agent in the same buffer. Fluids would be introduced through the inlets 37 and 37', and the buffer in which the active ingredient is incorporated would be introduced through the inlet 35. Flow out of the reaction unit is through an outlet 39.

FIG. 2 depicts a third preferred embodiment of a reaction unit for the device of the invention in which multiple cell lines are tested in a single series of test chambers 45 for response to gradients. The test chamber is bounded by two flow-through channels 51 that are operably connected to flow-through inlet channels 53 and 53' via fluid channels 52. Flow through fluid channels 52 is controlled by flow channel inlet valves 54 and 54' which are in turn controlled by flow channel inlet valve controllers 57 and 57' via flow channel inlet valve control channels 59 and 59'. In the embodiment of the reaction unit shown, the flow-through channels are essentially parallel at one of two widths over the long length of the test chamber. Moreover, the spacing between the ridges separating the test chambers are essentially equal. Therefore, the gradient is essentially repeated over the length of the test chambers. In the embodiment shown, cells are introduced through three inlets, 43, 43', and 43'' into the test chamber, and buffers are introduced through inlet port 55. Fluid flows out of the test chamber via outlet 47. The number of cell inlets is not a limitation of the embodiment of the invention.

EXAMPLES

It should be appreciated that the invention should not be construed to be limited to the examples that are now described; rather, the invention should be construed to include any and all applications provided herein and all equivalent variations within the skill of the ordinary artisan.

Example 1

Fabrication of a Device for Formation of Stable Gradients and Cell Imaging

The device was made using standard soft lithography techniques. The method of fabrication of the device is not a limitation of the invention.

Elastomeric devices have been developed for use in biological studies (for review see Xia and Whitesides 2003. *Electrophoresis* 24:3563-3576). Such devices can be biocompatible and can be prepared relatively easily and inexpensively by methods well known to those skilled in the art (See e.g., reviews Whitesides et al., 2001. *Ann. Rev. Biomed. Eng.* 3:335-373, incorporated herein by reference). Elastomeric devices made by the process of soft lithography are produced by casting of polydimethylsulfoxide (PDMS) or other silicone rubber onto micromachined molds or coated silicone wafers patterned using contact lithography, however, other materials and methods can be used.

Briefly, the fluid and control layers were separately printed at about 100% scale at high resolution onto transparencies to create a mask. Small variations in mask scale may be used to account for PDMS cast shrinkage during the fabrication procedure. The precise magnification may vary depending on the exact materials and methods used for fabrication of the device. Such modifications are well within the ability of those skilled in the art. Each mask was applied to a silicon wafer coated with photoresist and exposed to UV light, thereby transferring the pattern onto wafer by contact lithography. For elevated structures, positive photoresist is applied to the wafer, and exposed areas are removed using a chemical developer. For relatively tall structures, a negative mask and negative photoresist are used and unexposed areas are removed using a chemical developer. Methods of design and fabrication of complex structures using serial rounds of contact lithography are well known to those skilled in the art.

For the device of the invention, a negative master mold for the control layer was made by conventional contact lithography. A silicon wafer was spin coated with a 50 micron layer of SU-8 2050 resist (Microchem, Boston, Mass.) and patterned with UV light through a high resolution negative transparency mask. A master mold for the flow layer of channels was fabricated in a two step process. First, a 5 micron thick layer of SU-8 2005 photoresist was spun onto a silicon wafer and patterned with a different negative mask from the control layer. Next the wafer was spin-coated with a 25 micron thick layer of positive photoresist AZ100 (Clariant, Charlotte, N.C.) and exposed to w-light through a positive photomask. After development to remove the exposed areas, the AZ100 relief was rounded by 30 minutes of baking on a 140° C. hotplate. Flow-through channels of other z-dimensions were formed in a similar fashion. Test and flow through channels were fabricated using negative photoresist to create square channels of a defined height to facilitate flow patterning, whereas connection channels were formed using a positive, flowable photoresist to create rounded channels. Fluid flow through rounded channels is far more effectively controlled by the valves of the control layer than square or trapezoidal channels.

Using the method of Unger et al. (2000) elastomeric layers can be readily assembled to create channels in a first, bottom "flow layer" that can be regulated by elastomeric valves in a second, top "control layer." Valves are created where a control channel crosses a round, bottom-layer flow channel. The thin membrane between the two channels can be deflected by hydraulic actuation using a syringe or other device. When pressure is applied by passing air or other pressurized fluid through a control channel within the control layer, the membrane deflects downward to close off flow in the flow channel. Because the width of the control channel can be varied, and membrane deflection depends on dimensions, it is possible to have a control channel pass over a number of flow channels and actuate only a selection of flow channels. Tolerance in channel and valve sizes is largely dependent on ratios between the width of the valve/control channel and the fluid channel. Such considerations are well known to those skilled in the art. Guidance regarding the tolerance of the size of fluid channels, control channels, and valves can be found in Studer et al. (2004 *J. Appl. Phys.* 95: 393-398). Using such a layered design, miniaturized, elastomeric, computer-controlled microfluidics devices have been developed. Thorsten et al. (2002)

PDMS polymer mixed with a curing agent at a 5:1 ratio was cast thickly (about 5 mm) onto the control layer mold, and PDMS mixed with a curing agent at a 20:1 ratio was spincast thinly (about 35 microns thick) onto the fluid layer mold. Both casts were partially cured to create grooves and channels in the desired patterns. The control layer PDMS cast was then drilled to create valve controller openings, cleaned, and assembled onto the fluid layer PDMS cast. The two layers were bonded to each other by further curing. The resulting monolithic PDMS slab was drilled to create inlet and outlet ports, cleaned and reversibly bonded to glass to create the final device with the control layer on top of the fluid layer, and the fluid layer attached to the glass with the openings in the fluid layer facing towards the glass. This allows for removal of the glass to facilitate cleaning of the device so that it can be cleaned, rebounded, and reused.

Example 2

Figure 1C:
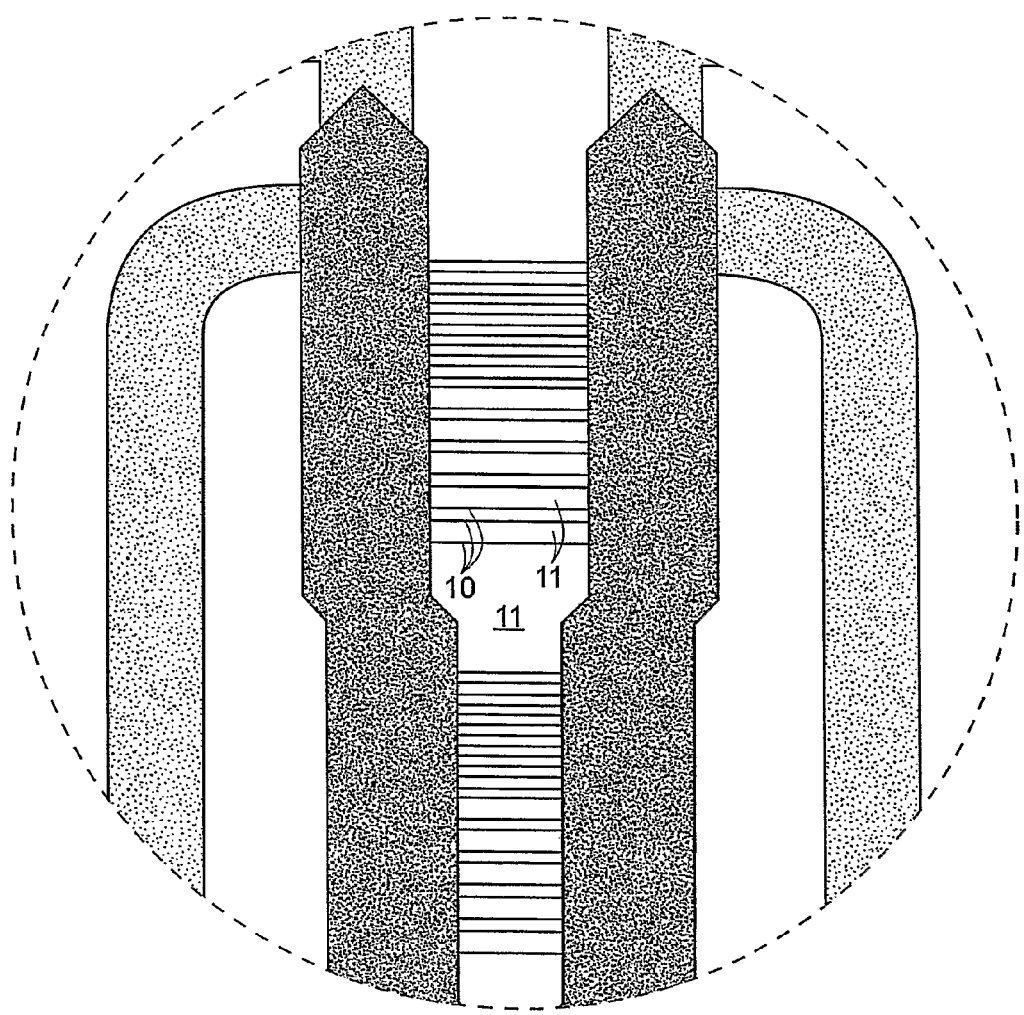
FIG. 1C is an enlarged view of a portion of the microfluidics device between the flow-through channels of FIG. 1A showing details of the test chambers.

Analysis of Response of A-Type Yeast to Exposure to a Gradient of Alpha-Factor Demonstrated Multi-Stability in Underlying Gene Regulation in Pheromone Response Using a device of the invention such as that shown in FIG. 1, analysis of phenotypic dose response in single cells was performed. Yeast cells were grown in YPD media to mid-log phase, and concentrated 10-fold before loading into syringes. The maximum pheromone concentrations used in the experiments was typically 75-100 nM, with varying minimum and maximum ranges for specific experiments. Pheromone diffusion was estimated by fluorescence imaging of the diffusion of Alexa Fluor dye 555 Hydrozide (Molecular Probes), with the MW of approximately 1150 Da (cf. 1684 Da MW of the α-factor), which was used at the concentration of 5 µM. Solutions of cells, pheromone and dye were put into modified 1 ml syringes, to which external air pressures could be applied. The syringes were connected to Tygon tubing (Cole Parmer, ID 0.02") caped by a metallic tip tightly inserted into the chip inlet. Syringes were then mounted on sliding platforms and fixed at different heights to control hydrostatic pressure at the inlets and outlets. Plain water was used for the valve inlet syringes.

The channels were initially filled with plain YPD medium. Cells were then introduced through one of the middle inlets into the chamber by generating a cross-flow of the medium with the desired cell densities through the chambers. The cross-flow was stopped by closing the control valves with 15 psi of external pressure. The flow through the 'side' channels (and thus gradient formation) was initiated by applying 0.36 psi relative pressure (approximately 10" height difference of the corresponding syringes).

Images were acquired using the Nikon Eclipse TE2000-U inverted epi-fluorescence microscope, using 20× (evaluation of the gradient values), and 100× (oil immersion; evaluation of yEGFP fluorescence) objectives. Phase contrast images were taken with automatic exposure control, whereas most fluorescence measurements involved manually specified fixed exposure times. Typical gradient measurements using Alexa Fluor 555 dye were obtained using red filter (G-2 E/C, 540/25 excitation wavelength) at a fixed exposure time of 1 sec, whereas yEGFP-mediated fluorescence was obtained using the green filter (YEL-GFP HQ, 500/20 excitation wavelength) at fixed exposure times of 3 secs. Pheromone concentrations and gradients were estimated from the diffusion profiles of the Alexa 555 dye (1150 Da), assuming that the maximum fluorescence observed at the edge of a chamber during an experiment was equal to that of the higher α-factor concentration solution fed into the chip. Whenever necessary, uneven field illumination was corrected for in gradient calculations, as follows. Within an image of a region of a test chamber that is expected to have uniformly bright fluorescence, at least 100 points are chosen uniformly and their fluorescence values are fitted to a two-dimensional function of the form: $f(x, y)=c_0+c_1 \cdot x+c_2 \cdot y+c_3 \cdot x^2+c_4 \cdot y^2+c_5 \, xy$. Calculation of the correction coefficients c0-c5 allowed us, for each position on the x-y plane, to assign a normalization factor based on the ratio of the maximum fluorescence value in the image and the predicted fluorescence value of the function $f(x,y)$ at that position. Subsequently, every gradient image is normalized such that each pixel is multiplied by the corresponding normalization factor Yeast phenotypes displayed in response to pheromone can be quite diverse. In addition to forming multiple projections or undergoing prolonged chemotropism at higher pheromone concentrations ('shmooing' or SM phenotype), cells at lower concentrations can undergo cell cycle arrest without formation of a shmoo (CCA phenotype), or, at yet lower concentrations, display no detectable response, continuing cell division ('budding' or BD phenotype). Within the microfluidic device, pheromone gradients with concentrations ranging from 0 to up to 100 nM were generated within multiple test chambers. Although the expected general distribution of phenotypic responses across the pheromone gradient was recapitulated, surprisingly, distinct phenotypes often co-existed in cell subpopulations exposed to the same concentrations of pheromone. Specifically, in the range of 1540 nM, the percentages of budded (BD), cell cycle arrest (CCA) and SM cells were comparable. Additionally, within this concentration range, cells that reverted from SM to BD phenotype were observed ('reverted from shmooing' or RS phenotype). These results suggested the existence of a range of α-factor concentrations, where the decision between assuming a specific phenotype might critically depend on some stochastically defined internal features controlling underlying biochemical reactions.

Co-existence of clearly identifiable BD, CCA, SM and RS phenotypes suggested presence of multi-stability in the underlying gene regulation network. To investigate the possibility for multi-stability in the pheromone response pathway, a mathematical model was constructed incorporating the activity of the MAPK, the pheromone-response specific transcription factor Ste12 and a Ste12 target gene. The model took into account up-regulation of expression of FUS3, STE12 and FUS1 by activated Ste12, genes known to be involved in the pheromone response pathway in yeast. Analysis of the model suggested that non-linear autoregulation of STE12 can lead to a combination of switch-like and graded regions in the dose response curves of transcription of FUS3 and FUS1. The existence of the bi-stable switch in the dose response also implied the presence of a hysteresis effect, whereby relatively higher FUS3 and FUS1 expression levels were expected in the switch region, if the pheromone concentration was decreased rather than increased to a given level.

To validate the model predictions, cells expressing Fus3-yEGFP and Fus1-yEGFP fusion proteins were generated by genomic integration of yEGFP at the locus of interest. For quantification of gene expression in response to varying pheromone concentrations, single cells introduced into individual test chambers were allowed to divide and thus eventually form clusters of adjacent cells. Additionally, cell clusters naturally formed by cell adhesion during introduction of cells into the chip. We analyzed multiple cell clusters (3-11 cells per cluster at the beginning of the experiment), each exposed to approximately the same α-factor concentration. Six hours following exposure of cells to 0-75 nM pheromone gradient, the nuclear Fus1-yEGFP signal generally increased, displaying a clear bimodal response in the 15-45 nM pheromone concentration range. Since cells in the same cluster frequently exhibited different phenotypic responses, clusters were further sub-classified into groups of cells displaying one of the BD/CCA/SM/RS phenotypes. Strikingly, the Fus1-yEGFP expression levels in BD, CCA and RS cells were statistically indistinguishable, whereas the difference between SM cells and cells of all other phenotypes, found in the bimodal region was highly significant (approximately 1.7-fold). The dose response results were similar for Fus3-yEGFP expression, but the bimodality was severely reduced due to high levels of basal Fus3 expression. These results were recapitulated in cells expressing yEGFP (rather than the fusion Fus1-yEGFP protein) under the control of FUS1 promoter, further suggesting that the underlying mechanism of bi-modal FUS1 expression is operational on the gene transcription level, rather than through post-transcriptional Fus1 modifications.

Bimodal responses are often a result of a combination of a switch-like behavior arising from bi-stability in response and a considerable stochasticity in distribution of key molecules across the cell population, allowing the cells to explore both available steady states in response to a given input. By contrast, fully deterministic systems displaying bi-stability are invariably 'locked' in one of the available steady states, depending on whether it is achieved by increasing or decreasing the input to a given value, leading to hysteresis. Stochasticity in the response is thus predicted to reduce the hysteresis effect, making the history of how the steady states are achieved less important. Hysteresis was studied in FUS3 and FUS1 transcription, by keeping cells in high uniform pheromone concentration (75 nM) for 4 hrs. and then imposing the usual graded pheromone concentration profile for additional 4 hrs. The initial pre-incubation invariably resulted in shmoo formation by all cells and maximal Fus1-yEGFP and Fus3-yEGFP expression. Following graded reduction of the pheromone concentrations, cells responded by either retaining the SM phenotype (higher pheromone concentrations) or resuming cell division, ultimately displaying a mixture of BD and RS phenotypes (lower pheromone concentrations). Bi-modal gene expression profiles were again observed and correlated with the presence of SM phenotype. The results indicated that, indeed, the expression levels of Fus1-yEGFP and Fus3-yEGFP were virtually indistinguishable at any pheromone concentration, regardless of whether it was raised or decreased to a particular value. However, one important feature of hysteresis remained: the SM cells were present at much lower concentrations of the pheromone in response to gradient formation by reduction from a high pheromone concentration, compared to the opposite case. This effect confirmed that, in agreement with the mathematical model, the underlying system is hysteretic and thus truly bi-stable.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A microfluidic device for formation and maintenance of gradients comprising:
    at least one reaction unit having a series of test chambers each having a depth, the test chambers being flanked by a first flow-through channel and a second flow-through channel, wherein the flow-through channels have a deeper depth than the test chambers, and each flow-through channel is connected to at least one inlet port and at least one outlet port.

2. The microfluidic device of claim 1, wherein the depth of the test chambers is less than about one half of the depth of the flow-through channels.

3. The microfluidic device of claim 1, wherein the depth of the test chambers is less than about one fifth of the depth of the flow-through channels.

4. The microfluidic device of claim 1, wherein the depth of the test chambers is less than about one tenth of the depth of the flow-through channels.

5. The microfluidics device of claim 1, wherein fluid flow resistance is higher in the test chambers than in the flow-through channels.

6. The microfluidic device of claim 1, wherein the depth of the test chamber is about 1 micron to about 20 microns.

7. The microfluidic device of claim 1, wherein the depth of the flow-through channels is about 25 microns to about 150 microns.

8. The microfluidic device of claim 1, further comprising at least one valve to control flow of fluid through at least one of the flow-through channels.

9. The microfluidic device of claim 8, wherein the valve is actuated through a controller that is operably connected to the valve via a connection channel.

10. The microfluidic device of claim 1, wherein the space between the first flow-through channel and the second flow-through channel is rectangular in shape in a plane of the flow-through channels.

11. The microfluidic device of claim 1, wherein a side of the first flow-through channel and a side of the second flow-through channel adjacent to the test chambers are essentially parallel.

12. The microfluidic device of claim 1, wherein the device is composed of a biocompatible elastomer.

13. The microfluidic device of claim 12, wherein the device is composed of polydimethylsulfoxide (PDMS), polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), or polytertrafluoroethylene (Teflon).

14. The microfluidic device of claim 1, wherein the device is optically clear.

15. The microfluidic device of claim 1, wherein the device is gas permeable.

16. The microfluidics device of claim 1, wherein the device provides for gradient generation and/or maintenance by having essentially no flow of fluid in the region of gradient generation.

17. The microfluidics device of claim 1, wherein the flow-through channels are minor-symmetric with respect to each other.

18. A microfluidic device for formation and maintenance of gradients comprising:
at least one reaction unit having a series of test chambers each having a depth, the test chambers being flanked by a first flow-through channel and a second flow-through channel, wherein the flow-through channels have a deeper depth than the test chambers, and each flow-through channel is operably connected to at least one inlet port, and at least one outlet port is operably connected to the flow-through channels, further comprising at least one port operably connected to the test chambers via a connection channel for delivery of cells into the test chambers.

19. A microfluidic device for formation and maintenance of gradients comprising: at least one reaction unit having a series of test chambers each having a depth, the test chambers being flanked by a first flow-through channel and a second flow-through channel, wherein the flow-through channels have a deeper depth than the test chambers, and each flow-through channel is operably connected to at least one inlet port, and at least one outlet port is operably connected to the flow-through channels, wherein the space between the first flow-through channel and the second flow-through channel is trapezoidal in shape in a plane of the flow-through channels.

20. A microfluidic device for formation and maintenance of gradients comprising:
at least one reaction unit having a series of test chambers each having a depth, the test chambers being flanked by a first flow-through channel and a second flow-through channel, wherein the flow-through channels have a deeper depth than the test chambers, and each flow-through channel is operably connected to at least one inlet port, and at least one outlet port is operably connected to the flow-through channels, wherein the flow-through channels merge downstream from the test chambers.

21. A microfluidic device for formation and maintenance of gradients comprising:
at least one reaction unit having a series of test chambers each having a depth, the test chambers being flanked by a first flow-through channel and a second flow-through channel, wherein the flow-through channels have a deeper depth than the test chambers, and each flow-through channel is operably connected to at least one inlet port, and at least one outlet port is operably connected to the flow-through channels, further comprising at least one cell inlet port and at least one cell outlet port operably connected to the series of test chambers.

22. A method of exposing cells to a gradient in a reaction unit with essentially no flow comprising:
closing fluid flow to flow-through channels of the reaction unit of claim 21;
introducing at least one cell through at least one cell inlet port to at least one test chamber in the reaction unit;
introducing a first fluid into a first flow-through channel and a second fluid into a second flow-through channel in the reaction unit; and
allowing the first fluid and the second fluid to flow through the flow-through channels to the outlet port.

23. A microfluidic device for formation and maintenance of gradients comprising:
at least one reaction unit having a series of test chambers each having a depth, the test chambers being flanked by a first flow-through channel and a second flow-through channel, wherein the flow-through channels have a deeper depth than the test chambers, and each flow-through channel is operably connected to at least one inlet port and at least one outlet port, further comprising at least one port operably connected to the test chambers via a connection channel for delivery of cells into the test chambers.

* * * * *